United States Patent
Ohrbom et al.

(10) Patent No.: US 6,624,279 B2
(45) Date of Patent: *Sep. 23, 2003

(54) WATER-SOLUBLE CARBAMATE MATERIALS

(75) Inventors: Walter H. Ohrbom, Hartland Township, MI (US); David J. Law, Livonia, MI (US); Patricia A. Herrel, Hartland Township, MI (US)

(73) Assignee: BASF Corporation, Southfield, MI (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/042,820

(22) Filed: Jan. 9, 2002

(65) Prior Publication Data

US 2002/0103319 A1 Aug. 1, 2002

Related U.S. Application Data

(60) Continuation-in-part of application No. 10/002,807, filed on Nov. 2, 2001, and a continuation-in-part of application No. 09/970,752, filed on Oct. 4, 2001, now Pat. No. 6,566,476, which is a division of application No. 09/316,591, filed on May 21, 1999, now Pat. No. 6,346,591.

(51) Int. Cl.$^7$ .............................................. C08G 18/06
(52) U.S. Cl. ................... 528/52; 428/423.1; 428/474.4; 428/500; 525/452; 525/456; 525/509
(58) Field of Search ........................ 428/423.1, 474.4, 428/500; 525/509, 452, 456; 528/52

(56) References Cited

U.S. PATENT DOCUMENTS

| | | | |
|---|---|---|---|
| 5,336,566 A | 8/1994 | Rehfuss | 428/524 |
| 5,356,669 A | 10/1994 | Rehfuss et al. | 427/407.1 |
| 5,451,656 A | 9/1995 | Menovcik et al. | 528/288 |
| 5,508,379 A | 4/1996 | Menovcik et al. | 528/367 |
| 5,512,639 A | 4/1996 | Rehfuss | 428/524 |
| 5,532,061 A | 7/1996 | Menovcik et al. | 428/423.1 |
| 5,639,828 A | 6/1997 | Briggs et al. | 525/208 |
| 5,693,723 A | 12/1997 | Green | 525/481 |
| 5,693,724 A | 12/1997 | Green | 525/481 |
| 6,262,297 B1 | 7/2001 | Clements et al. | 560/157 |
| 6,403,709 B2 | 6/2002 | Ramesh et al. | 525/95 |
| 2002/0010254 A1 | 1/2002 | Ramesh et al. | 524/401 |
| 2002/0132921 A1 | 9/2002 | Ramesh et al. | 525/88 |

FOREIGN PATENT DOCUMENTS

| WO | WO 00/26313 | 5/2000 |
|---|---|---|
| WO | WO 00/71505 | 5/2000 |
| WO | WO 01/44391 | 6/2001 |

OTHER PUBLICATIONS

Swaminathan Ramesh et al., USSN 09/747,473, filed Dec. 22, 2000, entitled "Water–based Coating composition having carbamate–melamine cross–linking method of preparing the same, and a cured film thereof" pp. 1–39, and the abstract.

Primary Examiner—Fred Zitomer
(74) Attorney, Agent, or Firm—Anna M. Budde

(57) ABSTRACT

The invention provides water-soluble, β-hydroxy carbamate-functional materials and coating compositions, especially waterborne coating compositions, containing the carbamate-functional materials. The invention further provide a coating prepared from the coating composition and a coated substrate, especially an automotive substrate, having the coating thereon.

20 Claims, No Drawings

WATER-SOLUBLE CARBAMATE MATERIALS

CROSS-REFERENCE TO RELATED APPLICATIONS

This application is a continuation-in-part of U.S. patent application Ser. No. 09/970,752, filed Oct. 4, 2001, now U.S. Pat. No. 6,566,476 which is a divisional of U.S. patent application Ser. No. 09/316,591, filed May 21, 1999 and now U.S. Pat. No. 6,346,591, entitled "Monomer and Polymerization Process" and a continuation-in-part of U.S. patent application Ser. No. 10/002,807, filed Nov. 2, 2001, entitled "Water- and Organic-Soluble Carbamate Material," the disclosures of each of which are incorporated herein by reference.

FIELD OF THE INVENTION

This invention concerns water-soluble carbamate-functional materials and curable coating compositions containing such materials, especially waterborne coating compositions containing such materials.

BACKGROUND OF THE INVENTION

Carbamate-functional materials have found particular utility in coating compositions as crosslinkable resins. Curable coating compositions utilizing carbamate-functional resins are described, for example, in U.S. Pat. Nos. 5,693,724, 5,693,723, 5,639,828, 5,512,639, 5,508,379, 5,451,656, 5,356,669, 5,336,566, and 5,532,061, each of which is incorporated herein by reference. These coating compositions can provide significant advantages over other coating compositions, such as hydroxy-functional acrylic/melamine coating compositions. For example, the coatings produced using carbamate-functional resins typically have excellent resistance to environmental etch (also called acid etch). Environmental etch results in spots or marks on or in the coating that often cannot be rubbed out.

One drawback of coatings with carbamate-functional resins is that they tend to require more organic solvent to achieve acceptable viscosity and for application. Carbamate-functional materials prepared from an isocyanurate of a diisocyanate, for example, are generally advantageous as an additive resin or principal resin in a coating composition, but these materials increase the viscosity of the coating composition so that more solvent is required. Coatings with higher amounts of organic solvent produce more regulated emissions during application.

Aqueous coating compositions have gained prominence due to the regulations on organic emissions. Such coatings have tended to be water-sensitive, however, because of the presence of the hydrophilic groups used to disperse the binder resins or surfactants, such as polyether-based surfactants, that remain in the coating film as low molecular weight, hydrophilic materials.

It would be advantageous to provide a water-soluble, carbamate-functional material for a coating composition that would not have water-sensitivity in a cured coating.

SUMMARY OF THE INVENTION

The invention provides a water-soluble, carbamate-functional materials and coating compositions, especially waterborne coating compositions, containing the carbamate-functional materials. The invention further provides a coating prepared from the coating composition and a coated substrate, especially an automotive substrate, having the coating thereon. The carbamate-functional materials of the invention have a sufficient number of β-hydroxy carbamate groups to be soluble in water. The carbamate materials may be dissolved in water at ambient temperature or warm water, with the water being heated up to perhaps about 50° C. The β-hydroxy carbamate groups have the isomeric structures

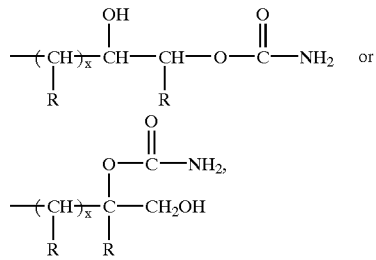

wherein each R is independently hydrogen, methyl, or ethyl and x is an integer of 1 to 3. Preferably, R is in each case a hydrogen and x is 1.

In one embodiment, the water-soluble, carbamate-functional materials may be represented by a structure

in which B represents β-hydroxy carbamate groups having the above structures; L represents a linking group formed by a hydrogen acceptor group; C represents an n-functional central moiety; and n is a positive integer. The carbamate groups are primary carbamate groups, i.e. there are two nitrogen hydrogens.

The central moiety C has up to about 5 carbon atoms per β-hydroxy carbamate group, preferably up to about 4.5 carbons per β-hydroxy carbamate group, more preferably up to about 4.0 carbons per β-hydroxy carbamate group, and still more preferably up to about 3.0 carbons per β-hydroxy carbamate group. In terms of the structure, the number of carbons of the C group may be represented by up to 5·n, preferably up to 4.5·n, more preferably up to 4.0·n, and still more preferably up to 3.0·n. For some applications, such as automotive topcoats, particularly automotive clearcoats, the C group is preferably aliphatic. In some preferred embodiments the C group includes an aliphatic ring.

DETAILED DESCRIPTION OF THE PREFERRED EMBODIMENTS

The following description of the preferred embodiment(s) is merely exemplary in nature and is in no way intended to limit the invention, its application, or uses.

In one embodiment, the water-soluble, carbamate-functional materials may be represented by a structure

in which B represents β-hydroxy carbamate groups having the structures

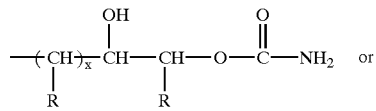

-continued

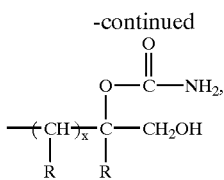

wherein each R is independently hydrogen, methyl, or ethyl, preferably hydrogen and x is an integer of 1 to 3, preferably 1; L represents a linking group formed by a hydrogen acceptor group; C represents an n-functional central moiety; and n is a positive integer, preferably at least two.

Suitable examples of the linking group L include, without limitation,

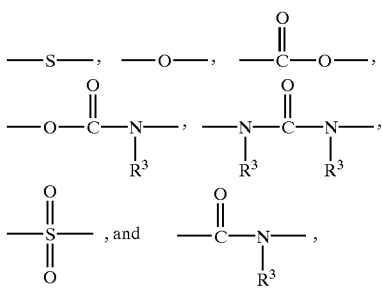

with one free bond of each group connected to B and the other free bond connected to C.

In one embodiment of the invention, the water-soluble, carbamate-functional material may be a homopolymer having a monomer unit represented by the structure

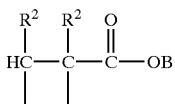

in which each $R^2$ is independently H or methyl and B is as defined above, or a monomer unit

in which B is as defined above.

The water-soluble carbamate-functional material may also be a copolymer having the monomer unit just described and having a fraction of different monomer units, particularly hydrophilic monomer units, in an amount so that the copolymer is water-soluble.

The β-hydroxy carbamate polymer may be the polymerization product of a monomer prepared by reacting a glycidyl-group containing polymerizable monomer first with carbon dioxide to convert the oxirane group to a cyclic carbonate group, and then with ammonia or a primary amine to convert the cyclic carbonate group to a β-hydroxy carbamate group. Examples of suitable oxirane group-containing polymerizable monomers include, without limitation, glycidyl acrylate, glycidyl methacrylate, glycidyl crotonate, and allyl glycidyl ether. Oxirane groups can be converted to carbamate groups by first converting to a cyclic carbonate group by reaction with $CO_2$. This can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, $KI$) preferably in combination with crown ethers, tin octoate, calcium octoate, and the like.

The cyclic carbonate group is reacted with ammonia or a primary amine. The primary amine preferably has up to four carbons, e.g. methyl amine. Preferably, the cyclic carbonate is reacted with ammonia. The ammonia may be aqueous ammonia (i.e., $NH_4OH$). The reaction ring-opens the cyclic carbonate to form a β-hydroxy carbamate monomer.

The polymerization of the monomer preferably is carried out in water or in an a mixture that includes water. The β-hydroxy carbamate monomer may be polymerized in the presence of free-radical initiators or with a redox initiator system. Useful initiators and redox initiator systems are well-known. The polymerization may be carried out without solvent or in an organic or aqueous medium. In a preferred embodiment, the β-hydroxy carbamate monomer is polymerized in an aqueous medium, preferably without any organic solvent or with a minor amount (up to about 10% by weight of the aqueous medium) of a polar solvent such as methanol, tetrahydrofuran, propylene glycol monomethyl ether, or other water-soluble or water-miscible solvents. The β-hydroxy carbamate monomer may be dissolved in water along with the initiating system and polymerized at a suitable temperature for the initiating system.

In an alternative embodiment, a homopolymer or copolymer including β-hydroxy carbamate units may be prepared by including the corresponding cyclic carbonate monomer and forming the carbamate group from the carbonate group at some time during the polymerization of the corresponding cyclic carbonate monomer. For example, a primary amine or ammonia can be charged to the polymerization reactor and react with the cyclic carbonate group during the polymerization. The reactor can be pressurized for ammonia or a gaseous primary amine. The ammonia or primary amine could also be added during the polymerization reaction.

Examples of homopolymers and copolymers of the β-hydroxy carbamate monomer useful for coating compositions are those that have weight average molecular weights of from about 5000 to over a million.

In another embodiment, the carbamate-functional compound of the invention may have a structure

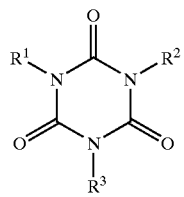

in which each of $R^1$, $R^2$, and $R^3$ is independently

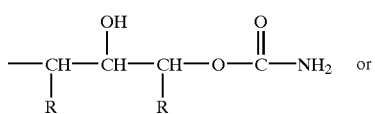

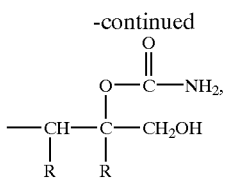

wherein R is hydrogen, methyl, or ethyl.

This water-soluble β-hydroxy carbamate compound may be prepared by reacting triglycidyl isocyanurate first with carbon dioxide to convert the oxirane groups to cyclic carbonate groups, and then with ammonia to convert the cyclic carbonate group to a β-hydroxy carbamate group. The reactions proceed in the same way as for the monomer synthesis already described. Triglycidyl isocyanurate is commercially available or may be prepared by reaction of isocyanuric acid with an epihalohydrin, in particular epichlorohydrin.

In yet another embodiment, the water-soluble carbamate functional compound of the invention may have as C structures selected from alkylene groups having up to about six carbon atoms, especially butylene, pentylene, hexylene, and cyclohexylene; and

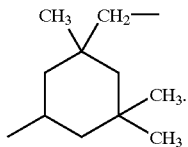

Further examples of β-hydroxy carbamate compounds of the invention may be prepared from glycidol carbonate, which has the structure

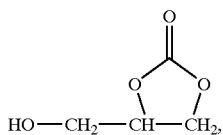

by reacting the hydroxyl group with a compound having a functional group reactive with hydroxyl and then by reacting the product with ammonia to convert the cyclic carbonate group to a β-hydroxy carbamate group. Glycidol carbonate is commercially available or may be prepared by reaction of glycidol with carbon dioxide, using such conditions as already described. Glycidol in turn may be prepared by reaction of allyl alcohol with peroxide. Alternatively, the alcohol group of one of the precursors to glycidol carbonate, either allyl alcohol or glycidol, may be reacted with the compound having a functional group reactive with hydroxyl before synthesis of the carbonate group and then carbamate group. This may be advantageous when the carbonate group may react with the compound having the functional group reactive with hydroxyl, for example if an esterification reaction is contemplated.

Examples of groups reactive with hydroxyl groups include, without limitation, acid groups, anhydride groups, isocyanate groups, lactones, oxirane (epoxide) groups, halides, and combinations of these. The reactions may be carried out under conditions typical for reactions of such groups with hydroxyl-functional compounds.

The allyl alcohol, glycidol, or glycidol carbonate may, for example, be reacted with a carboxylic acid-functional or anhydride-functional compound having up to about 5 carbon atoms per carboxylic acid group. Examples of suitable carboxylic acid and anhydride compounds include, without limitation, monocarboxylic acids such as butanoic acid; hydroxycarboxylic acids such as dimethylolpropionic acid; polycarboxylic acids such as phthalic acid, isophthalic acid, terephthalic acid, alkyl-substituted phthalic, isophthalic, and terephthalic acids; maleic acid, fumaric acid, itaconic acid, malonic acid, tetrahydrophthalic acid, hexahydrophthalic acid, and alkyl-substituted partially or fully hydrogenated phthalic, isophthalic, and terephthalic acids.

The esterification reaction can be conducted under typical esterification conditions, for example at temperatures from room temperature up to about 150° C., and with catalysts such as, for example, calcium octoate, metal hydroxides like potassium hydroxide, Group I or Group II metals such as sodium or lithium, metal carbonates such as potassium carbonate or magnesium carbonate (which may be enhanced by use in combination with crown ethers), organometallic oxides and esters such as dibutyl tin oxide, stannous octoate, and calcium octoate, metal alkoxides such as sodium methoxide and aluminum tripropoxide, protic acids like sulfuric acid, or $Ph_4SbI$. The reaction may also be conducted at room temperature with a polymer-supported catalyst such as Amerlyst-15® (available from Rohm & Haas) as described by R. Anand in *Synthetic Communications,* 24(19), 2743–47 (1994), the disclosure of which is incorporated herein by reference.

The allyl alcohol, glycidol, or glycidol carbonate may also be reacted with an isocyanate-functional compound. Examples of suitable isocyanate-functional compounds include, without limitation, monofunctional isocyanate compounds and polyisocyanates having up to about 5 carbons atoms per isocyanate group. Suitable examples of these include, without limitation, ethylene diisocyanate, 1,2-diisocyanatopropane, 1,3-diisocyanatopropane, 1,6-diisocyanatohexane (hexamethylene diisocyanate or HMDI), 1,4-butylene diisocyanate, cyclohexane-1,3- and -1,4-diisocyanate, 1,4-methylene bis-(cyclohexyl isocyanate), isophorone diisocyanate (IPDI), the various isomers of tolylene diisocyanate, 4,4'-dibenzyl diisocyanate, and 1,2,4-benzene triisocyanate, the dimers and trimers of these (including biurets, allophanates, and isocyanurates), and so on.

The reaction of the allyl alcohol, glycidol, or glycidol carbonate with the isocyanate-functional compound can be conducted under typical conditions for forming urethanes, for example at temperatures from room temperature up to about 150° C., and with catalysts such as, for example, tin catalysts including dibutyl tin dilaurate, dibutyl tin oxide, and the like.

The coating composition further includes at least one crosslinker reactive with functionality, preferably including the carbamate functionality, of the β-hydroxy carbamate material. Particularly useful crosslinkers include, without limitation, materials having active methylol or methylalkoxy groups, such as aminoplast crosslinking agents or phenol/formaldehyde adducts. Examples of preferred curing agent compounds include, without limitation, melamine formaldehyde crosslinkers, including monomeric or polymeric melamine resin and partially or fully alkylated melamine resin, urea resins, and methylol ureas such as urea formaldehyde resin, alkoxy ureas such as butylated urea formaldehyde resin. Another suitable crosslinking agent is tris (alkoxy carbonylamino) triazine (available from Cytec Industries under the trademark TACT). Other useful crosslinkers include, without limitation, polyisocyanates and blocked polyisocyanates, curing agents that have siloxane groups, aldehyde groups, and anhydride groups. The curing agent may be combinations of these, particularly combinations that include aminoplast crosslinking agents. At least one crosslinker with functionality reactive with active hydrogens of the β-hydroxy carbamate compound is included. Aminoplast resins such as melamine formaldehyde resins or urea formaldehyde resins are especially preferred. Water-soluble aminoplast resins for aqueous coating compositions are known. These include high imino-content melamine formaldehyde resins and fully methoxylated melamine formaldehyde resins.

In preferred embodiments, the crosslinker is at least about 5%, more preferably at least about 10% by weight of the nonvolatile vehicle. It is also preferred for the crosslinker to be up to about 40%, more preferably up to about 30% by weight of the nonvolatile vehicle. The crosslinker is preferably from about 5% to about 40%, more preferably from about 10% to about 35%, and still more preferably from about 15% to about 35% by weight of the nonvolatile vehicle.

The coating composition may include further crosslinkable compounds, resin, and/or polymers, preferably those that have active hydrogen functionality. Examples of additional compounds, resins, and/or polymers that may optionally be included are other carbamate- or hydroxyl-functional materials, including acrylic polymers, polyurethanes, and polyesters.

The coating composition used in the practice of the invention may include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluene sulfonic acid, dinonyinaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

Although aqueous coating compositions that are free of regulated volatile organic compounds are preferred, a solvent may optionally be utilized in the coating composition used in the practice of the present invention. In general, the solvent can be any organic solvent and/or water. In one preferred embodiment, the solvent is a polar organic solvent. More preferably, the solvent is selected from polar aliphatic solvents or polar aromatic solvents. Still more preferably, the solvent is a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

The coating composition according to the invention is preferably utilized in an automotive or industrial high-gloss coating and/or as the clearcoat of an automotive composite color-plus-clear coating. High-gloss coatings as used herein are coatings having a 20° gloss (ASTM D523) or a DOI (ASTM E430) of at least 80.

The coating composition may also be formulated as a pigmented coating, such as for a basecoat coating or a primer coating. In this case, the coating composition further includes a pigment or filler material. The pigment may be any organic or inorganic compounds or colored materials, metallic or other inorganic flake materials such as pearlescent mica flake pigments or metallic flake pigments such as aluminum flake, and other materials of kind that the art normally includes in such coatings. Examples of typical fillers are talc and barytes. Pigments and other insoluble particulate compounds such as fillers are usually used in the composition in an amount of 1% to 100%, based on the total solid weight of binder components (i.e., a pigment-to-binder ratio of 0.1 to 1).

Additional agents, for example surfactants, stabilizers, wetting agents, rheology control agents, dispersing agents, adhesion promoters, UV absorbers, hindered amine light stabilizers, etc. may be incorporated into the coating composition. While such additives are well-known in the prior art, the amount used must be controlled to avoid adversely affecting the coating characteristics.

Coating compositions can be coated on the article by any of a number of techniques well-known in the art. These include, for example, spray coating, dip coating, roll coating, curtain coating, and the like. For automotive body panels, spray coating is preferred.

When the coating composition according to the invention is used as the clearcoat of a composite color-plus-clear coating, the pigmented basecoat composition may any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

Basecoat polymers may be self-crosslinkable, or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

The coating compositions described herein are preferably subjected to conditions so as to cure the coating layer. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 90° C. and 180° C. The first compounds according to the present invention are preferably reactive even at relatively low cure temperatures. Thus, in a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following example. The examples are merely illustrative and do not in any way limit the scope of the invention as described and claimed. All parts are parts by weight unless otherwise noted.

EXAMPLES

EXAMPLE 1

Preparation of β-Hydroxy Carbamate Propyl Methacrylate

A methanolic solution of the cyclic carbonate of glycidyl methacrylate (available from Dow Corp., Midland, Mich.) was prepared by dissolving 1095.4 grams of the cyclic carbonate of glycidyl methacrylate in 1140 grams of methanol. The dissolved monomer was reacted with anhydrous ammonia, which was bubbled into the solution over a period of about 2.75 hr. The initial temperature was about 17° C., and the exotherm peaked at about 30° C. and was controlled by holding the reactor in a cooling bath. After the ammonia add was ended, the reactor was closed. The contents of the flask were stirred for an additional 5 hrs. When infrared analysis showed no remaining carbonate, 0.1 gram of MEHQ was added to stabilize the monomer and the methanol and unreacted ammonia are distilled under vacuum to yield a solid product having a slight pink color from the MEHQ.

The solid product (1147 g) is dissolved in 751.8 grams of water to yield a 60.4% nonvolatile solution.

EXAMPLE 2

Preparation of a Homopolymer of β-Hydroxy Carbamate Propyl Methacrylate

A reactor was charged with 193.4 grams of deionized water and heated to 80° F. under a nitrogen atmosphere. After the water had reached 80° C., a mixture of 306.2 grams of the solution of Example 1 and 11.2 grams of ammonium persulfate was added over a period of one hour. A solution of 0.9 grams of ammonium persulfate in 10 grams of deionized water was added over about 15 minutes. The reaction mixture was held for about 45 minutes longer, then cooled. The product was an aqueous polymer solution that had a faint haze.

EXAMPLE 3

Preparation of a Coating Composition Containing the Homopolymer of β-Hydroxy Carbamate Propyl Methacrylate A coating composition was prepared by combining 21.3 grams of the aqueous homopolymer solution of Example 2 with 6.1 grams of hexamethoxymethylated melamine and 0.2 gram of an acid catalyst (70% solution of dodecylbenzene sulfonic acid). The mixture was drawn down 7 mm thick over a steel panel primed with electrocoat primer. The drawn down coating layer was allowed to flash to 10 minutes at 180° F. to aid in evaporation of the water. The coating layer was baked for 30 minutes at 285° F. The resulting cured film was hard and passed solvent resistance tests of 200 double rubs with methyl ethyl ketone and a one-minute soak in methyl ethyl ketone.

The coating composition of Example 3 was examined for 7 mil drawdowns cured at 285° F. for 30 minutes on the substrates shown in the table below.

| | | |
|---|---|---|
| Parts of homopolymer (NV) | 12.9 | 12.9 |
| Parts of Resimene 747 (from Solutia) | 6.1 | 6.1 |
| Parts of dodecylbenzene sulfonic acid | 0.14 | 0.14 |
| Substrate | Electrocoat primed panel | Steel panel |
| 200 MEK double rubs | pass | pass |
| 1 minute MEK Soak | no effect | no effect |

EXAMPLE 4

Preparation of β-Hydroxy Carbamate Propyl Methacrylate

A mixture of 200 parts by weight of the cyclic carbonate of glycidyl methacrylate in 50.7 parts by weight of deionized water was charged to a reaction vessel and 59.6 parts by weight of concentrated ammonium hydroxide (28 to 32% ammonia) were slowly added. The two phase system slowly converted into one phase as the carbonate monomer reacted to form the β-hydroxy carbamate propyl methacrylate product.

EXAMPLE 5

Preparation of Water Soluble Carbamate Compound

In a suitable reactor, 2000 grams of a 70% by weight solution of the tricarbonate of triglycidyl isocyanurate (obtained from Vantico: structure

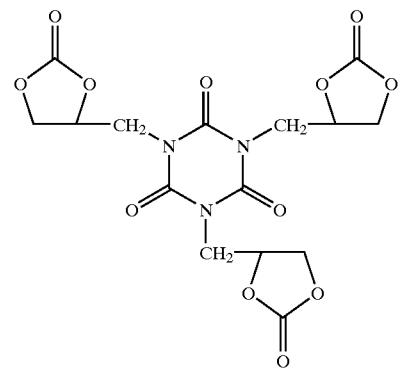

in water was reacted with 1000 grams of concentrated ammonium hydroxide. Ammonia gas was then bubbled into the reaction mixture. When the reaction was complete, excess ammonium hydroxide and a portion of the water were removed by vacuum stripping. Water was then added to obtain a 77.5% nonvolatile by weight solution of the tricarbamate product having having a structure

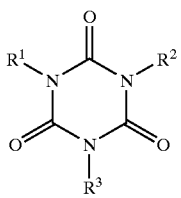

wherein each of $R^1$, $R^2$, and $R^3$ is independently

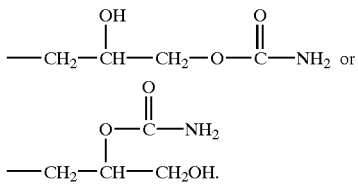

A clear coating composition was prepared by mixing together 100 grams of the tricarbamate product, 77.8 grams of CYMEL® 327 (a fully methylated melamine, 90% nonvolatile in butanol), 5.6 grams of a solution of dodecylbenzene sulfonic acid (25% active), 18.3 grams of N-methyl pyrrolidinone, and 0.8 grams of a silicone additive. The viscosity of the coating composition was 200 centipoise at 400 $s^{-1}$. The VOC of the coating composition was 1.0 lb./gal.

The clear coating composition was applied over a flashed (dried, but not cured) layer of a basecoat coating composition over an electrocoat primed steel panel in the following way. A 4 mil wet drawdown of the basecoat composition was applied on the electrocoat primed steel panel. The basecoat layer drawdown was flashed for five minutes at 140° F. A 4 to 5 mil wet drawdown layer of the clear coating composition was applied in a layer perpendicular to the basecoat layer drawdown. The panel was flashed for 10 minutes at 110° F., then baked for 20 minutes at 280° F. The baked basecoat layer was 0.8 mils and the baked clearcoat layer was 2.0 to 2.4 mils.

The baked clearcoat layer passed a crosshatch test for adhesion to the basecoat layer. The basecoat/clearcoat composite coating had a hardness of 37 Knoops on a Tukon hardness machine.

EXAMPLE 6

Preparation of Water Soluble Carbamate Compound

In a suitable reactor, a mixture of 16.0 parts by weight anhydrous butyl acetate, 15.7 parts by weight 1,6-hexylene diisocyanate, and 0.02 parts by weight of dibutyl tin dilaurate was heated under an inert atmosphere to 43° C. Then, keeping the reaction temperature below 80° C., 22.0 parts by weight of glycerine carbonate was slowly added. Once all of the isocyanate functionality was consumed, the reaction slurry mixture was cooled to 35° C. and 42.6 parts by weight of methanol was added. Ammonia was then bubbled into the reaction mixture until all of the cyclic carbonate was consumed. The excess ammonia and solvent was then removed by vacuum distillation. Water was then added to provide a 67.5% by weight solution of the reaction product.

The invention has been described in detail with reference to preferred embodiments thereof. It should be understood, however, that variations and modifications can be made within the spirit and scope of the invention.

What is claimed is:

1. A water-soluble, carbamate-functional material having a structure

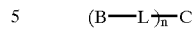

in which B represents β-hydroxy carbamate groups, each independently having a structure

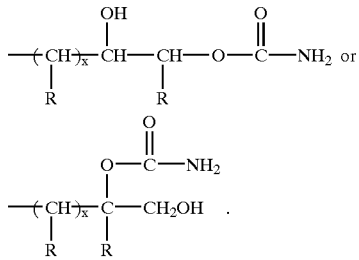

wherein each R is independently hydrogen, methyl, or ethyl and x is an integer of 1 to 3; L represents a linking group formed by a hydrogen acceptor group; C represents an n-functional central moiety; and n is a positive integer.

2. An aqueous composition, comprising water and the compound of claim 1.

3. A coating composition, comprising the compound of claim 1 and at least one crosslinker reactive with carbamate functionality.

4. A coating composition according to claim 3, wherein the crosslinker is a melamine formaldehyde resin.

5. The coating composition according to claim 3, wherein the coating composition is aqueous.

6. The coating composition according to claim 3, wherein the composition includes from about 5% to about 70% of the compound of claim 1.

7. The coating composition according to claim 3, wherein the composition includes from about 20% to about 60% of the compound of claim 1.

8. The coating composition according to claim 3, wherein the composition is a clearcoat coating composition.

9. A coating on a substrate, comprising a layer of the cured composition of claim 3.

10. A composite coating on a substrate, comprising a layer of basecoat coating and a layer of the cured clearcoat coating composition of claim 8.

11. A water-soluble, carbamate-functional material having a sufficient number of β-hydroxy carbamate groups having a structure

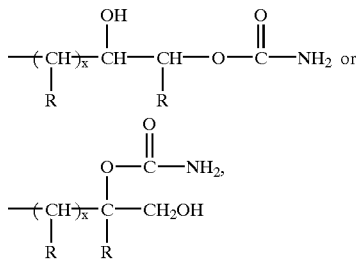

wherein each R is independently hydrogen, methyl, or ethyl and x is an integer of 1 to 3, to be soluble in water at a temperature of 50° C. or less.

12. An aqueous composition, comprising water and the compound of claim 11.

13. A coating composition, comprising the compound of claim 11 and at least one crosslinker reactive with carbamate functionality.

14. A coating composition according to claim 13, wherein the crosslinker is a melamine formaldehyde resin.

15. The coating composition according to claim 13, wherein the coating composition is aqueous.

16. The coating composition according to claim 13, wherein the composition includes from about 5% to about 70% of the compound of claim 11.

17. The coating composition according to claim 13, wherein the composition includes from about 20% to about 60% of the compound of claim 11.

18. The coating composition according to claim 13, wherein the composition is a clearcoat coating composition.

19. A coating on a substrate, comprising a layer of the cured composition of claim 13.

20. A composite coating on a substrate, comprising a layer of basecoat coating and a layer of the cured clearcoat coating composition of claim 18.

* * * * *